United States Patent [19]

Elger et al.

[11] Patent Number: 5,095,010

[45] Date of Patent: * Mar. 10, 1992

[54] ANTIGESTAGENS, GLUCOCORTICOIDS AND PROSTAGLANDINS FOR INDUCTION OF LABOR OR FOR TERMINATION OF PREGNANCY

[75] Inventors: Walter Elger; Sybille Beier, both of Berlin, Fed. Rep. of Germany

[73] Assignee: Schering Aktiengesellschaft, Berlin and Bergkamen, Fed. Rep. of Germany

[*] Notice: The portion of the term of this patent subsequent to Dec. 2, 2003 has been disclaimed.

[21] Appl. No.: 611,619

[22] Filed: Nov. 13, 1990

Related U.S. Application Data

[63] Continuation of Ser. No. 790,020, Oct. 22, 1985, abandoned.

[30] Foreign Application Priority Data

Oct. 22, 1984 [DE] Fed. Rep. of Germany ....... 3438994

[51] Int. Cl.$^5$ .................. A61K 31/565; A61K 31/57; A61K 31/58; A61K 31/557
[52] U.S. Cl. .................................. 514/171; 514/179; 514/180; 514/935
[58] Field of Search ........................ 514/171, 180, 179

[56] References Cited

U.S. PATENT DOCUMENTS

| | | | |
|---|---|---|---|
| 3,743,730 | 7/1973 | Adams | 514/180 |
| 3,775,539 | 11/1973 | Anderson | 514/180 |
| 3,856,955 | 12/1974 | Anderson | 514/180 |
| 3,892,855 | 1/1975 | Short | 514/177 |
| 3,966,927 | 6/1976 | Binninger | 514/180 |
| 4,060,620 | 11/1977 | Bauman et al. | 514/171 |
| 4,452,794 | 6/1984 | Kort et al. | 514/179 |
| 4,626,531 | 12/1986 | Elger et al. | 514/171 |
| 4,686,103 | 8/1987 | Anderson | 514/171 |
| 4,870,066 | 9/1989 | Edgerton et al. | 514/180 |

FOREIGN PATENT DOCUMENTS 3438994 4/1986 Fed. Rep. of Germany ...... 514/171

OTHER PUBLICATIONS

Chemical Abstracts, vol. 84 (1976) #84673s; Evans et al.

Liggins et al., "A Controlled Trial of Antepartum Glucocorticoid Treatment for Prevention of the Respiratory Distress Syndrome in Premature Infants," *Pediatrics*, vol. 50, No. 4, Oct. 1972.

W. Elger et al., "Studies on the Mechanisms of Action of Progesterone Antagonists," J. Steroid Biochem., vol. 25, No. 5B, pp. 835-845, 1986.

G. C. Liggins et al., "Control of Parturition in Man," Biology of Reproduction 16, 39-56 (1977).

*Primary Examiner*—Shep K. Rose
*Attorney, Agent, or Firm*—Millen, White & Zelano

[57] ABSTRACT

Combination products containing an antigestagen, a glucocorticoid and a prostaglandin are suitable for combined use in inducing labor or terminating pregnancy.

16 Claims, No Drawings

ANTIGESTAGENS, GLUCOCORTICOIDS AND PROSTAGLANDINS FOR INDUCTION OF LABOR OR FOR TERMINATION OF PREGNANCY

This application is a continuation of application Ser. No. 06/790,020, filed Oct. 22, 1985, now abandoned.

BACKGROUND OF THE INVENTION

This invention relates to a combination product for combined use in induction of labor or termination of pregnancy.

To avert danger to mother and/or child, it is sometimes necessary to induce birth artificially or prematurely terminate pregnancy. Surgical techniques and pharmacological methods are available for this purpose.

A good pharmacological method is vaginal or intramuscular application of prostaglandins. This is used if pregnancy is terminated in the 1st or 2nd trimester of the pregnancy (*Contraception* 1983, Vol. 27, 51-60, and *Int. J. Gynaecol. Obstet.* 1982, Vol. 20, 383-386). The advantages of prostaglandins include the ease of application and the ability to use them over a long period of pregnancy. The disadvantages of prostaglandins include acute side effects such as pains and nausea; moreover, the success rate in the case of termination of pregnancy in advanced phases of pregnancy is not more than 90%, even after lengthy treatment with prostaglandins.

Another possibility of terminating a pregnancy is to apply an antigestagen (*Med. et Hyg.* 1982, Vol. 40, 2087-2093). Antigestagens are tolerated better than prostaglandins, but compared with prostaglandins they have greater latency and individual variability with regard to the commencement of effect. In animal tests, in which muscular effects on the uterus play a decisive role, they trigger abortions with a latency of several days. In these tests, some antigestagens otherwise very effective, are effective in only a portion of the animals, even at the highest dosages tested.

In German patent application P 33 37 450.3 (U.S. Ser. No. 660,358 of Oct. 12, 1984, which disclosure is incorporated by reference herein), there is a description of how disadvantages typical of PG and AG can be avoided by using prostaglandins (PG) and antigestagens (AG) jointly for termination of pregnancy. In this connection, the amounts of prostaglandin and antigestagen when used in combination can be considerably reduced in comparison to the customary amounts, it being possible to increase the success rate of terminations of pregnancy even more.

SUMMARY OF THE INVENTION

It is an object of this invention to provide yet a further improved method and product for termination of pregnancy.

Upon further study of the specification and appended claims, further objects and advantages of this invention will become apparent to those skilled in the art.

These objects have been achieved by the finding that a further increase in the success rate can be surprisingly achieved by administration of a glucocorticoid (GC) in addition to the PG and AG. The fact that this increase was especially great in precisely those cases in which the addition of a prostaglandin to an antigestagen did not lead to a great improvement in the abortion rate, is especially favorable.

DETAILED DISCUSSION

With this three-component product comprising a prostaglandin, antigestagen and glucocorticoid, means is available for therapeutic termination of pregnancy or induction of labor with the highest rates of success, e.g., in mammals, including humans. It permits methods of treatment than can be better standardized and which facilitate clinical application. As a result of the product in accordance with this invention, the time that passes from the beginning of treatment until expulsion is clearly shortened by more reliable and faster activation of the resting muscles of the pregnant uterus. Adequate therapeutic effects are therefore achieved with comparatively low doses of AG and PG due to the high effectiveness of the three-component combination in accordance with the invention and the comparatively short treatment times until therapeutic success is achieved.

The antigestagen and glucocorticoid are preferably used separately and simultaneously and/or chronologically staggered (sequentially). The prostaglandin, antigestagen and glucocorticoid can also be used together in one dosage unit. Suitable weight ratios of prostaglandin to glucocorticoid are about 1:10 to 1:3,000, preferably 1:10 to 1:300, and of prostaglandin to antigestagen about 1:10 to 1:10,000, preferably 1:100 to 1:500.

These weight ratios are based on appropriate values for the preferred active ingredients, i.e., sulprostone as the prostaglandin, 11$\beta$-[(4-N,N-dimethylamino)-phenyl]-17$\beta$-hydroxy-17$\alpha$-propinyl-4,9(10)-estradien-3-one as the anti-gestagen and dexamethasone as the glucocorticoid. Corresponding weight ratios for any other ingredients can be readily determined using fully conventional techniques, e.g., involving differential potency studies using conventional protocols.

Prostaglandins suitable for use in accordance with the invention include all prostaglandins suitable for termination of pregnancy; i.e., prostaglandins of the E and F-series in particular. Non-limiting examples include:

prostaglandin $E_2$,
prostaglandin $F_{2\alpha}$,
prostaglandin E-derivatives like
  16-phenoxy-$\omega$-17,18,19,20-tetranor-$PGE_2$-methylsulfonylamide (sulprostone),
  16,16-dimethyl-trans-$\Delta^2$-$PGE_1$-methylester (Gemeprost),
  9-deoxo-16,16-dimethyl-9-methylene-$PGE_2$ (Metenenprost),
prostaglandin F-derivatives like
  15-methyl-$PGF_{2\alpha}$-methylester, (5Z,13E)-(9R,11R,15R)-9-chloro-11,15-dihydroxy-16,16-dimethyl-5,13-prostadienoic acid (DE-OS 29 50 027),
  (5Z,13E)-(9R,11R,15R)-11,15-dihydroxy-9-fluoro-16-phenoxy-17,18,19,20-tetranor-5,13-prostadienoic acid (DE-OS 31 26 924),
  (5Z,13E)-(9R,11R,15R)-11,15-dihydroxy-16,16-dimethy-9-fluoro-15,13-prostadienoic acid (DE-OS 31 26 924),
  (5Z,13E)-(9R,11R,15R)-9-bromo-11,15-dihydroxy-16-phenoxy-17,18,19,20-tetranor-5,13-prostadienoic acid (DE-OS 31 48 743),
  (5Z,13E)-(9R,11R,15R)-9-bromo-11,15-dihydroxy-16,16-dimethyl-5,13-prostadienoic acid (DE-OS 31 48 743).

The prostaglandins can be used in amounts comprising less than those otherwise customary for termination of pregnancy. The amount to be used in accordance with the invention depends, inter alia, on the hormone level, the duration of the pregnancy and the type of application. When sulprostone is used as the prostaglandin, 0.02 to 3.0 mg per day will usually be sufficient. The application can, for example, be local, topical, enteral or parenteral. In the case of intra-muscular injection and/or intravenous infusion, for example, amounts of approximately 1.0 to 3.0 mg of sulprostone per day are suitable. In the case of local (topical) application, extra-amniotically or intravaginally for example, approximately 0.02 to 0.5 mg of sulprostone per day are useful. One unit dose of prostaglandin generally contains 0.02 to 0.5 mg of sulprostone or a biologically equivalent amount of another prostaglandin. For topical application it is also possible to use transdermal systems such as skin plasters. Instead of sulprostone it is possible, in accordance with the invention, to use biologically equivalent amounts of other prostaglandins. These bioavailability equivalent amounts can be determined routinely and conventionally, e.g., by performing differential potency studies using fully routine pharmacological protocols, e.g., W. Elger, *Animal Reproduction Science* 2 (1979), 133.

Suitable antigestagens include all compounds that have a strong affinity for the gestagen receptor (progesterone receptor) while not displaying any gestagenic activities of their own. The following steroids, for example, are possible as competitive progesterone antagonists:

11β-[(4-N,N-dimethylamino)-phenyl]-17β-hydroxy-17α-propinyl-4,9(10)-estradien-3-one and 11β-[(4-N,N-dimethylamino)-phenyl]-17β-hydroxy-18-methyl-17α-propinyl-4,9(10),16-estradien-3-one and 11β-[(4-N,N-dimethylamino)-phenyl]-17aβ-hydroxy-17aα-propinyl-D-homo-4,9(10),16-estratrien-3-one (European Patent Application 82400025.1 - Publication No. 0 057 115); furthermore 11β-p-methoxyphenyl-17β-hydroxy-17α-ethinyl-4,9-(10)-estradien-3-one (Steroids 37 (1981) 361–382);

11β-4,N,N-dimethylaminophenyl)-17α-hydroxy-17β-(3-hydroxy propyl)-13α-methyl-4,9-gonadien-3-one and 11β-[(4-N,N-dimethylamino)-phenyl]-17β-hydroxy-17α-(3-hydroxyprop-1-(Z)-enyl)-4,9(10)-estradien-3-one (German Patent application P 33 47 126.6).

Also suitable for use in this invention are antigestagens which antagonize the effect of gestagens per se, i.e., operate by a route different from competing with the gestagen receptor. Suitable such antigestagens include the derivatives of trilostane (U.S. Pat. No. 4,160,027).

The foregoing listing is exemplary only. Many other antigestagens can be used, e.g., as disclosed in *Fertility and Sterility* 40, 253 (1982), *Steroids* 37, 361 (1981).

The antigestagens are used, in accordance with the invention, in amounts that are generally lower than those otherwise customary for termination of pregnancy.

In general, 5 to 200 mg of 11β[(4-N,N-dimethylamino)-phenyl]-17β-hydroxy-17α-(3-hydroxyprop-1-(Z)enyl)-4,9(10)-estradiene-3-one or 11β-[(4-N,N-dimethylamino)-phenyl]-17α-hydroxy-17β-(3-hydroxy-propyl)-13α-methyl-4,9-gonadien-3-one per day or a biologically equivalent amount of another antigestagen will be sufficient. Precise dosages can be routinely determined using conventional techniques in view of this disclosure. The mentioned bioequivalent amounts can be determined conventionally and routinely. e.g., by performing differential potency studies using fully routine pharmacological protocols, e.g., *Fertility and Sterility* 40, 253 (1982), *Steroids* 37, 361 (1981).

Suitable glucocorticoids include all effective corticoids. A list of conventional corticoids can be found in E. Schroeder, C. Rufer, R. Schmiechen *"Pharmazeutische Chemie"*, Georg Thieme Verlag, Stuttgart (1982), p. 424. Non-limiting examples include prednisone, prednisolone, fluocortolone, triamcinolone, methylprednisolone, prednylidene, paramethasone, dexamethasone, betamethasone, beclometasone or fluprednylidene.

Suitable glucocorticoid dosages, e.g., in humans are 0.3 to 100 mg. In general, 0.3 to 10 mg of dexamethasone per day or a biologically equivalent amount of another glucocorticoid (e.g., 5 to 100 mg prednisone per day) will be sufficient. Bioequivalent amounts can be determined conventionally and routinely, e.g., by performing differential potency studies using fully routine pharmacological protocols, as discussed in, e.g., "Medicinal Chemistry, A Series of Monographs by G. De Stevens (Ed.) Vol. 13/1 *Antiinflammatory Agents* Vol. 1, Academic Press, New York et al 1974, pp. 245–293".

For the preferred oral application, it is possible to use, in particular, tablets, dragees, capsules, pills, suspensions or solutions that can be manufactured in the customary fashion with the additives and carrier substances commonly used in galenicals. For local or topical application, for example, it is possible to use vaginal suppositories or transdermal systems such as skin plasters. The galenic formulations are well known and analogous to those for the individual ingredients themselves.

Generally, a unit dose of antigestagen contains 5 to 200 mg of active ingredient and a unit dose of glucocorticoid contains 0.3 to 100 mg of active ingredient.

The joint treatment with prostaglandin, antigestagen and glucocorticoid usually takes place over 1 to 4, preferably 1 to 2 days, it being possible to apply the anti-gestagen and glucocorticoid preferably separately and simultaneously or chronologically staggered (sequentially). In sequential therapy, preferably, the antigestagen and glucocorticoid are first applied for 1 to 3 days and subsequently prostaglandin alone or prostaglandin and antigestagen/glucocorticoid together for 24 hours. It is further possible to first administer antigestagen or antigestagen/prostaglandin and subsequently prostaglandin/glucocorticoid or glucocorticoid alone.

The three active ingredients can also be applied in combination in one unit dose in one and the same vehicle (e.g., oleaginous solution like a benzyl benzoate/castor oil mixture). Other than as indicated herein, administration will be analogous to that of the known active ingredients alone.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight; unless otherwise indicated.

EXAMPLE 1

Composition of a Freeze-dried Sulprostone Formulation Per Ampoule

| | |
|---|---|
| 0.1 mg | sulprostone |
| 5.0 mg | polyvinylpyrrolidone (K value = 15–18) |
| 1.95 mg | tris(hydroxymethyl)aminomethane-hydrochloride (tremetamol.Hcl) (from 1.5 mg of tremetamol and 1N hydrochloric acid) |
| 7.05 mg | |

For dosage and application, the contents of the ampoule are dissolved with an isotonic sodium chloride solution for intra-muscular injection or intravenous infusion or extra-amniotical application.

Manufacture of the Dry Substance

Sulprostone is dissolved in distilled water by addition of a pre-cooled solution of polyvinylpyrrolidone and tremetamol. The pH value of the solution is set at 5.0 by addition of 1N hydrochloric acid with strong cooling. The solution is then filled to the necessary volume. The solution is dosed out in ampoules after filtration through a membrane filter.

The solution is then frozen by immersing the ampoules in a cooling mixture of acetone and dry ice, and immediately freeze-dried in a precooled freeze-drying installation for approximately 48 hours. After completion of the freeze-drying process the ampoules are immediately sealed.

EXAMPLE 2

Composition of a Film with Sulprostone for Vaginal Application

| | |
|---|---|
| 0.1 mg | sulprostone |
| 19.6 mg | hydroxypropyl cellulose |
| 0.32 mg | polyoxyethylene-polyoxypropylene polymers (Pluronic F 68 ®) |
| 20.02 mg | |

The length of the film is 3 cm.

EXAMPLE 3

Composition of a Film with Sulprostone for Buccal Application

| | |
|---|---|
| 0.3 mg | sulprostone |
| 9.16 mg | hydroxypropyl cellulose |
| 9.16 mg | cellulose fibers |
| 0.15 mg | polyoxyethylene-polyoxypropylene polymers (Pluronic F 68 ®) |
| 18.77 mg | |

The surface of the film is 1.2 by 1.2 cm.

EXAMPLE 4

Composition of a Tablet with Sulprostone for Vaginal Applications

| | |
|---|---|
| 0.1 mg | sulprostone |
| 238.9 mg | lactose |
| 110.0 mg | microcrystalline cellulose |
| 1.0 mg | magnesium stearate |
| 350.0 mg | |

EXAMPLE 5

Composition of Another Tablet with 11$\beta$-[(4-N,N-dimethylamino)-phenyl]-17$\beta$-hydroxy-17$\alpha$-(3-hydroxy-prop-1-(Z)-enyl)-4,9(10)-estradien-3-one for Oral Application

| | |
|---|---|
| 10.0 mg | 11$\beta$-[(4-N,N-dimethylamino)-phenyl]-17$\beta$-hydroxy-17$\alpha$-(3-hydroxy-prop-1-(Z)-enyl)-4,9(10)-estradien-3-one |
| 140.5 mg | lactose |
| 69.5 mg | corn starch |
| 2.5 mg | polyvinylpyrrolidone 25 |
| 2.0 mg | "Aerosil" |
| 0.5 mg | magnesium stearate |
| 225.0 mg | |

EXAMPLE 6

Composition of a Tablet with Dexamethasone for Oral Application

| | |
|---|---|
| 0.050 mg | dexamethasone |
| 76.515 mg | corn starch USP XVI |
| 36.000 mg | lactose |
| 6.000 mg | talcum |
| 1.400 mg | gelatine, white |
| 0.024 mg | "Nipagin M" ® (p-hydroxybenzoic acid methylester) |
| 0.011 mg | "Nipasol M" ® (p-hydroxybenzoic acid propylester) |
| 120.000 mg | |

Pharmacological Observations

For pilot tests on pregnant guinea pigs, sulprostone was selected as the model substance for the prostaglandin, 11$\beta$-[(4-N,N-dimethylamino)-phenyl]-17$\beta$-hydroxy-17$\alpha$-(3-hydroxy-prop-1-(Z)-enyl)-4,9(10)-estradien-3-one for the antigestagen, and dexamethasone for the glucocorticoid.

Description of Test

The tests were carried out on pregnant guinea pigs weighing approximately 800 g on the 42nd day of pregnancy (the second day of vaginal opening in the mating phase was calculated as the first day of pregnancy). Pregnancy was checked by palpation before the test began. The animals were treated with the combinations by daily injections on the 43rd and 44th day of pregnancy. For this purpose the test substances were dissolved in benzyl benzoate+castor oil (mixing ratio with sulprostone: 1+9; antigestagen 2+4.5; glucocorticoid 2+2.4) and the daily dose of 0.4 ml of sulprostone, 0.5 ml of antigestagen and 0.5 ml of glucocorticoid subcutaneously injected. Possible expulsion of the embryo was checked several times on the 50th day of the pregnancy. The uteri were inspected and the findings on the fetuses recorded.

AG/PG Combination

The combination of 10.0 mg/d of 11$\beta$-[(4-N,N-dimethylamino)-phenyl]-17$\alpha$-hydroxy-17$\beta$(3-hydroxypropyl)-13$\alpha$-methyl-4,9-gonadien-3-one injected subcutaneously with a marginally effective dose of 0.03 mg/d of sulprostone subcutaneously led after 24 hours to termination of pregnancy in the case of approximately 50% of the animals treated. With 10.0 mg of 11β-[(4-N,N-dimethylamino)-phenyl]-17β-hydroxy-17α(3-hydroxyprop)-1-(Z)-enyl)-4,9(10)-estradien-3-one as the antigestagen the corresponding value amounts of 0%. The abortions obtained after two injections with the AG/PG combination took place with a latency of 1 to 5 days after the beginning of treatment.

AG/PG/GC Combination

The combination of 10.0 mg/d of 11β-[(4-N,N-dimethylamino)-phenyl]-17α-hydroxy-17β(3-hydroxypropyl)-13α-methyl-4,9-gonadien-3-one injected subcutaneously with 0.3 mg/d s.c. of dexamethasone and 0.03 mg/d s.c. of sulprostone led within less than 24 hours, i.e. after only one injection, to an abortion rate of 100% (6/6).

With 10.0 mg of 11β-[(4-N,N-dimethylamino)-phenyl]-17β-hydroxy-17α(3-hydroxy-prop-1-(Z)-enyl)-4,9(10)-estradien-3-one as the antigestagen a much high abortion rate was achieved after 24 hours (60 to 70% in comparison with 0% with the corresponding AG/PG combination). Furthermore, the period of latency was considerably reduced (0.5 to 2.5 days).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inducing labor or abortion or otherwise terminating pregnancy in a pregnant guinea pig, human or other mammalian patient comprising administering to the patient 0.02-5 mg of an effective prostaglandin, 5-200 mg of an effective antigestagen, and 0.3-100 mg of effective glucocorticoid, applied simultaneously and separately, or simultaneously and jointly, or chronologically staggered, or sequentially over 1-4 days, in a weight ratio of prostaglandin to glucocorticoid of 1:10-1:3,000 and of prostaglandin to antigestagen of 1:10-1:10,000, the total amount of the combination of the prostaglandin, antigestagen and glucocorticoid being effective to terminate pregnancy, wherein the pregnancy termination rate exceeds that achieved by prostaglandin alone or by prostaglandin and antigestagen used together without a glucocorticoid, said amount of prostaglandin being less than otherwise customary for pregnancy termination.

2. A method according to claim 1, wherein the amount of the prostaglandin and the amount of the antigestagen are both lower than the amount at which each is effective to terminate pregnancy when used alone.

3. A method according to claim 1, wherein the total amount of the prostaglandin and the antigestagen is lower than the total amount of prostaglandin and antigestagen effective to induce abortion when the prostaglandin and antigestagen are used together without the glucocorticoid to induce abortion.

4. A method according to claim 1, wherein the prostaglandin, antigestagen and glucocorticoid are administered together in one dosage unit.

5. A method according to claim 1, wherein the prostaglandin is 0.2-0.5 mg of 16-phenoxy-ω-17,18,19,20-tetranor-PGE$_2$-methylsulfonylamide or a biologically equivalent amount of another prostaglandin.

6. A method according to claim 1, wherein the antigestagen is 5-200 mg of 11β-[(4-N,N-dimethylamino)-phenyl]-17β-hydroxy-17α-(3-hydroxyprop-1(Z)-enyl)-4,9(10)-estradien-3-one or a biologically equivalent amount of another antigestagen.

7. A method according to claim 1, wherein the antigestagen is 5-200 mg of 11β-[(4-N,N-dimethylamino)-phenyl]-17β-hydroxy-17α-(3-hydroxypropyl)-13α-methyl-4,9-gonadien-3-one or a biologically equivalent amount of another antigestagen.

8. A method according to claim 1, wherein the glucocorticoid is 0.3 to 1 mg of dexamethasone or a biologically equivalent amount of another glucocorticoid.

9. A method according to claim 1, wherein the prostaglandin is prostaglandin E$_2$, prostaglandin F$_{2\alpha}$, 16-phenoxy-ω-17,18,19,20-tetranor-PGE$_2$-methylsulfonylamide, 16,16-dimethyl-trans-Δ$^2$-PGE$_1$-methyl ester, 9-deoxo-16,16-dimethyl-9-methylene-PGE$_2$, 15-methyl-PGF$_{2\alpha}$-methyl ester, (5Z,13E)-(9R,11R,15R)-9-chloro-11,15-dihydroxy-16,16-dimethyl-5,13-prostadienoic acid, (5Z,13E)-(9R,11R,15R)-11,15-dihydroxy-9-fluoro-16-phenoxy-17,18,19,20-tetranor-5,13-prostadienoic acid, (5Z,13E)-(9R,11R,15R)-11,15-hydroxy-16,16-dimethyl-9-fluoro-5,13-prostadienoic acid, (5Z,13E)-(9R,11R,15R)-9-bromo-11,15-dihydroxy-16-phenoxy-17,18,19,20-tetranor-5,13-prostadienoic acid, or (5Z,13E)-(9R,11R,15R)-9-bromo-11,15-dihydroxy-16,16-dimethyl-5,13-prostadienoic acid.

10. A method according to claim 1, wherein the antigestagen is 11β-[(4-N,N-dimethylamino)-phenyl]-17β-hydroxy-17α-propinyl-4,9(10)-estradien-3-one, 11β-[(4-N,N-dimethylamino)-phenyl]-17β-hydroxy-18-methyl-17α-propinyl-4,9(10)-estradien-3-one, 11β-[(4-N,N-dimethylamino)-phenyl]-17aβ-hydroxy-17aα-propinyl-D-homo-4,9(10),16-estratrien-3-one, 11β-p-methoxyphenyl-17β-hydroxy-17α-ethinyl-4,9(10)-estradien-3-one, or 11β-(4-dimethylaminophenyl)-17α-hydroxyl-17β-(3-hydroxy-propyl)-13α-methyl-4,9-gonadien-3-one.

11. A method according to claim 1, wherein the glucocorticoid is prednisone, prednisolone, fluocortolone, triamcinolone, methylprednisolone, prednylidene, paramethasone, dexamethasone, betamethasone, beclometasone or fluprednylidene.

12. A method according to claim 1, wherein prostaglandin is 0.02-0.5 mg of 16-phenoxy-ω-17,18,19,20-tetranor-PGE$_2$-methyl-sulfonyl-amide; the antigestagen is 5-200 mg of 11β-[(4-N,N-dimethylamino)-phenyl]-17β-hydroxy-17α-(3-hydroxyprop-1(Z)-enyl-4,9(10)-estradien-3-one or the antigestagen is 5-200 mg of 11β-[(4-N,N-dimethylamino)-phenyl]-17α-hydroxyl-17β-(3-hydroxypropyl)-13α-methyl-4,9-gonadien-3-one; and the glucocorticoid is 0.3 to 1 mg of dexamethasone.

13. A method of claim 1, wherein the administration of the prostaglandin, the antigestagen and the glucocorticoid is performed simultaneously.

14. A method of claim 1, wherein the administration of the prostaglandin, the antigestagen, and the glucocorticoid is sequentially.

15. A method of claim 1, wherein the prostaglandin, the antigestagen and the glucocorticoid are administered in performed separate dosage units.

16. A method according to claim 1, wherein administration of the composition occurs over a period of one to two days.

* * * * *